United States Patent [19]
Sohr

[11] Patent Number: 5,920,606
[45] Date of Patent: Jul. 6, 1999

[54] APPARATUS USED IN TAKING WEIGHT-BEARING FOOT AND ANKLE X-RAYS

[76] Inventor: Tonia J. Sohr, 608 Sheridan Rd. No. 2, Evanston, Ill. 60202

[21] Appl. No.: 08/956,089

[22] Filed: Oct. 23, 1997

Related U.S. Application Data

[60] Provisional application No. 60/029,833, Oct. 28, 1996.

[51] Int. Cl.⁶ .................................................. G03B 42/02

[52] U.S. Cl. ........................................ 378/177; 378/208

[58] Field of Search ...................................... 378/177, 180

[56] References Cited

U.S. PATENT DOCUMENTS

| | | | |
|---|---|---|---|
| 3,293,430 | 12/1966 | Wustner | 378/177 |
| 3,633,028 | 1/1972 | Marino | 378/180 |
| 3,916,207 | 10/1975 | Reed | 378/177 |

*Primary Examiner*—Craig E. Church
*Attorney, Agent, or Firm*—Leo J. Aubel

[57] ABSTRACT

An apparatus for taking X-rays of a weight-bearing foot of a patient, said apparatus including a raised platform having a transparent top surface, steps leading up to said platform, and a drawer for positioning an X-ray film cassette beneath the transparent plate whereby a technician can visual determine the positioning of the cassette relative to the X-ray beam and the patient's foot.

4 Claims, 1 Drawing Sheet

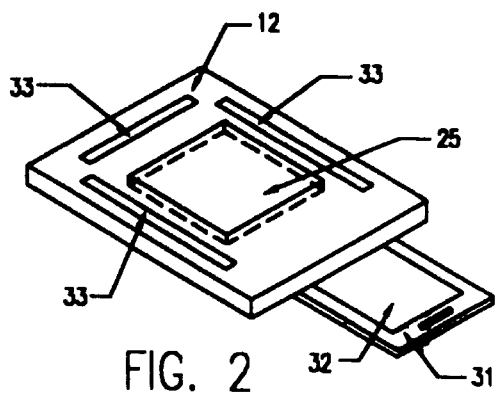
FIG. 1
FIG. 2
FIG. 3
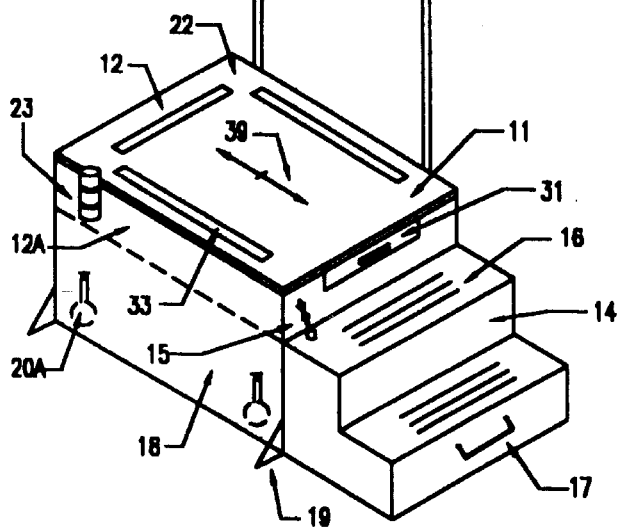
FIG. 4
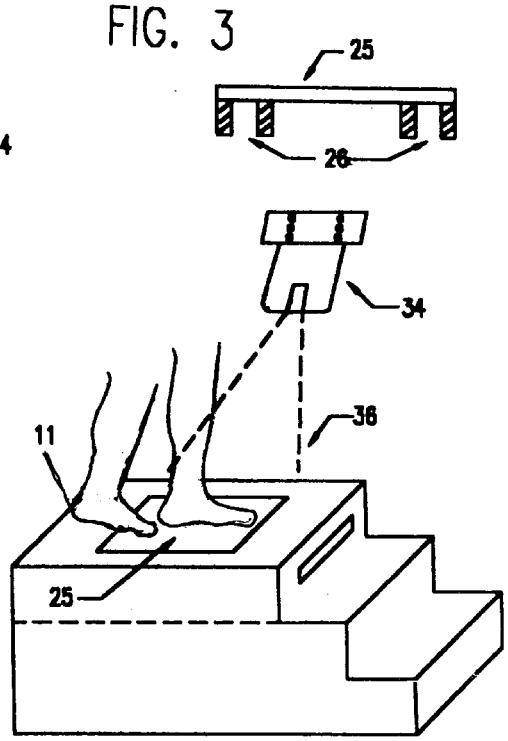
FIG. 5
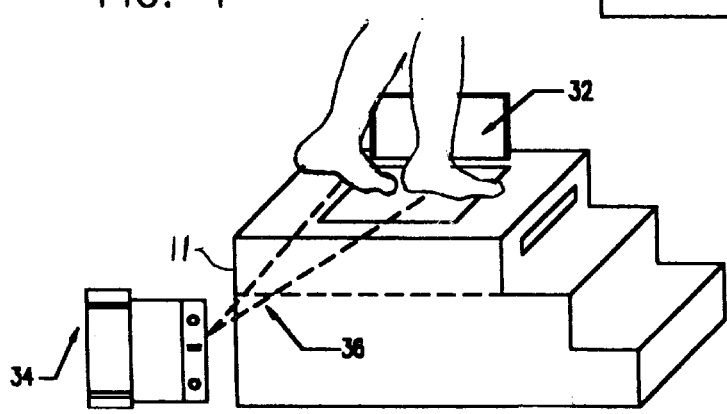
FIG. 6

APPARATUS USED IN TAKING WEIGHT-BEARING FOOT AND ANKLE X-RAYS

This application and invention claims the benefits and priority of U.S. Provisional Application No. 60/029,833 filed Oct. 28, 1996 in the name of the inventor and applicant herein.

BACKGROUND OF INVENTION

This invention relates to the art and procedure of taking X-rays of a patient's foot when the patient is standing. At present, it has been found that to obtain weight-bearing, anterior-posterior (AP) projections of a patient's foot (i.e., front-back), it is necessary to position the film cassette on the floor and have the patient stand directly on the film cassette. This procedure presents two principal problems. First, often the cassettes are damaged due to the weight of the patient, and secondly it is difficult to properly position the head of the X-ray machine carrying the X-ray tube to take an X-ray of the foot when the patient is standing on the floor. Accordingly, a present method of accomplishing the task is to use a step stool, and an adjustable cassette holder. A patient has to step up onto the step stool and the cassette holder has to be adjusted to the height of the step stool. Obviously for safety purposes, the stool cannot be too high off the floor, and some sort of support has to be found for the patient. In one known example, the stools used for patients to step onto are nine inches (9") high, while the center of the horizontal X-ray beam can be adjusted to about eighteen inches (18") off the floor at its lowermost position. It is difficult and dangerous for many patients to step up 18". The center of the X-ray beam should enter the foot at the arch, accordingly in the example just recited, the foot is not high enough off the floor for a properly positioned lateral foot radiograph. The same problem occurs in making radiographs of weight-bearing ankles.

SUMMARY OF INVENTION

The invention relates to a weight-bearing apparatus having a transparent plate for supporting the weight of a patient. The plate is mounted on a support platform, having retractable steps leading up to the plate. The platform includes a drawer beneath the transparent plate to receive a film. The transparent plate enables the technician operator to view the positioning of the cassette relative to the patient's foot for taking anterior-posterior projections of a patient's foot. Slots on the sides of the platform selectively receive film cassettes to enable the taking of lateral projections of the foot and ankle.

The foregoing features and advantages of the present invention will be apparent from the following more particular description of the invention. The accompanying drawings, listed hereinbelow, are useful in explaining the invention.

DESCRIPTION OF DRAWINGS

FIG. 1 is an isometric view of the inventive apparatus or device;

FIG. 2 is partial isometric top view of the apparatus to indicate the pullout drawer to accommodate the cassette, and slots for accommodating the film cassettes;

FIG. 3 is a front view partially in section to show the mounting of the transparent surface plate.

FIG. 4 is a view of an individual railing;

FIG. 5 is a view of the platform of the device indicating an X-ray source taking an anterior-posterior (AP) projection (X-ray exposure) of a patient's foot;

FIG. 6 is a view of the platform of the device indicating an X-ray source taking a lateral X-ray projection of a patient's foot.

DESCRIPTION OF INVENTION

FIG. 1 shows the inventive device or apparatus 11 that comprises a platform 12 on which a patient may stand for enabling the taking of weight-bearing foot and/or ankle X-rays. Apparatus or device 11 includes three closed sides 12A, and a front side having an opening to accommodate the steps 14. The interior frame of apparatus 11 is of standard design, and is omitted to maintain clarity in the drawings. In one embodiment, the platform is made of wood with a Formica laminate top surface. The platform is approximately 18 inches (18") in height and twenty-two inches by twenty-four inches (23"×24")in horizontal dimension. Other light but strong material may be used to make the device. The platform 12 is sufficiently sturdy to support the weight of a human patient, and for safety purposes is designed to support approximately 350 pounds, with a safety factor.

Retractable steps 14 extend under the surface of the platform 12 and can be pulled out by handle 17 to a position in front of the platform 12 for use, as shown in FIG. 1. In the extended position of the steps 14, the unit is forty-two inches (42") in length. Suitable detents (not shown) of any known type are provided to limit the outward movement of the steps 14. A locking pin 15 is provided to lock the steps 14 in their outward position to prevent the steps from moving when a patient is climbing onto or down from the platform 12. The steps 14 have standard type of corrugations 16 and/or anti-slip tape to prevent slippage. For storage, steps 14 are pushed into the space 18 under the platform 12. Outwardly angled feet 19 are affixed to the sides of device 11 for bracing purposes. Platform 12 includes retractable rollers or wheels 20 to permit the convenient movement or positioning of the platform. The rollers or wheels 20 are of any well known design that depress when a weight above a selected amount is placed on the platform.

One or two essentially identical support or guard rails or railings 20 and 21 of inverted U-shape design are mounted on respective side edges of the platform 12. The railings 20 and 21 are received in, and supported by, respective brackets 23 mounted on the sides the back of platform 12. Only one bracket is shown in FIG. 1, and railing 21 is shown in FIG. 4. The top surface of platform 12 which extends outwardly of the sides 12A is suitably grooved, as at 22, to accommodate the railings; for esthetic purposes the top surface of platform extends slight outwardly of sides 12A. When two railing are used they are conveniently positioned at right angles to each other, with one of the railings being mounted at the back side of platform 12, that is opposite the steps 14, and the other railing being mounted on one or the other side dependent on the position of the X-ray source. It has been found that the patient can grasp and hold onto one or both rails for support when climbing up the steps, and when he or she is standing on the platform, the rails serve to brace the patient as the foot is positioned to be X-rayed.

Importantly, a transparent plate or surface 25 comprises the top surface of platform 12. As shown in FIG. 1, in one embodiment, plate 25 is made of one half inch (½") thick polycarbonate (Lexan) plastic. A second embodiment of the invention plate 25 is shown in FIG. 2 and comprises a plate which is approximately eighteen inches (18") square and mounted to be the center of platform 12 and to be flush with the top surface of platform 12.

FIG. 3 is a partial section across plate 25 of FIG. 1. As shown in FIG. 3, plate 25 is firmly mounted on support members, which for example may comprise known 2"×4" lumber 26 or similarly strong material. For further reinforcement a metal bar reinforcement, not shown, extends on the front of platform 12, above the drawer opening. A cross-hair type of mark 39 may be imprinted on the plate 25 to indicate to the patient where to initially place his or her foot.

Platform 12 includes a pullout drawer 31 for receiving an X-ray film cassette or cassette 32. The cassette 32 is placed in a horizontal orientation in drawer 31. As shown in FIGS. 1 and 2, the drawer 31 can be pulled out toward the front of the platform 12 and is sufficiently large to accommodate film cassettes 11"×14" in size. Standard X-ray film cassettes are either 10"×12" or 11"×14" in size.

Platform 12 also includes rectangular slots 33 along its periphery to receive respective cassettes 32 in a vertical position. The slots 33 are formed in the three sides of the platform 12 other than the side from which the drawer 31 extends. It has been found that three slots 33 are convenient to enable the placing of a cassette 32 in a selected slot to accommodate the location of the X-ray source or tube 34 and the positioning of the patient, as will be described below.

Refer now to FIG. 5 which depicts the apparatus 11 in use to take and X-ray of a patient's foot 35 when the foot is bearing the weight of the patient. The procedure is initiated by having the patient climb the steps 14 onto the platform 12. In FIG. 5, a weight-bearing AP (anterior-posterior) projection (X-ray exposure) is to be taken of the patient's foot. The patient positions his foot 35 on the transparent plate 25. The film cassette 32 is placed in the drawer 31 and the drawer is pushed into position under the plate 25. The X-ray tube source 34 is then adjusted and angled down as necessary to position the expected emmission or X-ray beam 36 onto the foot 35. The radiologist can than visually inspect the proposed X-ray picture and can fine-tune the relative position of the cassette 32 in the drawer, the foot 35, and/or the position and angle of the X-ray tube 34.

If an X-ray exposure is desired to be at an angle rather than directly from front to back then the patients foot, the X-ray source and the cassette adjustments are conveniently and expeditiously made. In every case, the radiologist can visually determine the impingement of the X-ray beam and the required positioning of the cassette in drawer 31.

FIG. 6 depicts the taking of weight-bearing lateral radiograph of a patient's foot. As in the previous case, the patient positions his or her foot on the plate 25 which comprises the center of platform 12. In this application, the cassette is placed in one of the slots 33 to be in a vertical position. The X-ray tube 34 is lowered to a position which is approximately horizontally level with the patients foot. Since the platform 12 is about 18" high, most X-ray machines have a tube head that can be lowered to this height. The patient's foot can be turned or moved to take an exposure of at the desired angle. The multiple slots 33 permit the radiologist leeway in positioning the cassette 32 dependent on the location of the X-ray source and the particular X-ray which is desired.

While the invention has been particularly shown and described with reference to a particular embodiment thereof it will be understood by those skilled in the art that various changes in form and detail may be made therein without departing from the spirit and scope of the invention.

I claim:

1. An apparatus for facilitating the positioning of an X-ray source to provide X-ray beams to X-ray film cassettes to take selected X-rays of a weight-bearing foot of a patient comprising, a) a raised platform having a substantially level upper surface that permits a patient to stand thereon;

b) steps leading up to said platform;

c) railing means extending upwardly above said platform;

d) drawer means for receiving X-ray film cassettes, said drawer means positioned beneath said surface;

e) a visually transparent plate forming a portion of the upper surface of said platform and presenting an unobstructed view from externally of the platform to a cassette positioned in said drawer means, whereby the relative position of a cassette in said drawer means and the foot of a patient standing on said plate can be visually ascertained from externally of said platform to properly position the patient's foot and said cassette relative to said X-ray source.

2. Apparatus as in claim 1 wherein said railing comprise at least two support or guard rails in substantially perpendicular relation to extend upwardly from respective side edges of said platform.

3. An apparatus as in claim 1 wherein said platform is mounted on wheels that depress when a weight above a selected amount is placed on the platform to thus provide a secure stationary platform support when a patient supports the weight of his or her foot on the steps.

4. An apparatus for facilitating the positioning of an X-ray source to provide X-ray beams to X-ray film cassettes to take selected X-rays of a weight-bearing foot of a patient comprising, a) a raised platform having a substantially level upper surface that permits a patient to stand thereon;

b) steps leading up to said platform;

c) said steps being retractable to a position underneath said platform;

d) railing means extending upwardly above said platform;

e) means for receiving X-ray film cassettes, said receiving means extending beneath said surface;

f) a visually transparent plate forming a portion of the upper surface of said platform and presenting an unobstructed view from externally of the platform to a cassette positioned in said cassette receiving means, whereby the relative position of a cassette in said drawer means and the foot of a patient standing on said plate can be visually ascertained from externally of said platform to properly position the patient's foot and said cassette relative to said X-ray source.

\* \* \* \* \*